US00PP35979P3

(12) United States Plant Patent
Jones et al.

(10) Patent No.: US PP35,979 P3
(45) Date of Patent: Jul. 9, 2024

(54) ***SAMBUCUS* PLANT NAMED 'HYFJOLAIS'**

(50) Latin Name: *Sambucus nigra*
Varietal Denomination: HYFJOLAIS

(71) Applicants: John Jones, Newtown (GB); Maria Jones, Newtown (GB)

(72) Inventors: John Jones, Newtown (GB); Maria Jones, Newtown (GB)

( * ) Notice: Subject to any disclaimer, the term of this patent is extended or adjusted under 35 U.S.C. 154(b) by 342 days.

(21) Appl. No.: 17/947,300

(22) Filed: Sep. 19, 2022

(65) Prior Publication Data

US 2023/0210035 P1 Jun. 29, 2023

(30) Foreign Application Priority Data

Sep. 22, 2021 (QZ) ..... PBR 20212332

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

*Primary Examiner* — Keith O. Robinson
(74) *Attorney, Agent, or Firm* — Penny J. Aguirre

(57) ABSTRACT

A new cultivar of *Sambucus* plant named 'HYFJOLAIS' that is characterized by its short stem internodes, its leaves that are dark in color, its flowers that are distinct from foliage and white in color with burgundy and pink highlights, and its compact plant habit.

2 Drawing Sheets

Genus/species: *Sambucus nigra.*
Varietal denomination: 'HYFJOLAIS'.

CROSS-REFERENCE TO A RELATED APPLICATION

This application claims priority to European Community Plant Variety Office (CPVO) Plant Breeder's Rights Application No. 2021/2332 filed on Sep. 22, 2021, under 35 U.S.C. 119(f), the entire contents of which is incorporated by reference herein.

BACKGROUND OF THE INVENTION

The present invention relates to a new and distinct cultivar of *Sambucus nigra* and will be referred to hereafter by its cultivar name, 'HYFJOLAIS'. 'HYFJOLAIS' represents a new cultivar of Elderberry, a deciduous shrub grown for landscape use.

'HYFJOLAIS' was discovered by the Inventor in 2014 as a seedling growing in a container in Cefn Hyfryd, Powys, The United Kingdom. The containers had been planted with seeds collected from open pollinated plants of *Sambucus nigra* 'Eva' (U.S. Plant Pat. No. 15,575). The male parent is therefore unknown.

Asexual propagation of the new cultivar was first accomplished by the Inventor by softwood stem cuttings in 2014 in Cefn Hyfryd, Powys, The United Kingdom. Asexual propagation of the new cultivar by softwood stem cuttings has determined that the characteristics are stable and are reproduced true to type in successive generations.

SUMMARY OF THE INVENTION

The following traits have been repeatedly observed and represent the characteristics of the new *Sambucus*. These attributes in combination distinguish 'HYFJOLAIS' as a unique cultivar of *Sambucus.*

1. 'HYFJOLAIS' exhibits short stem internodes.
2. 'HYFJOLAIS' exhibits leaves that are dark in color.
3. 'HYFJOLAIS' exhibits flowers that are distinct from foliage and white in color with burgundy and pink highlights.
4. 'HYFJOLAIS' exhibits a compact plant habit.

The female parent plant of 'HYHOLAIS', 'Eva', differs from 'HYFJOLAIS' in having longer stem internodes, leaves that are lighter in color, and flowers that are lighter in color and less pink and burgundy tinged, and a less compact plant habit. 'HYFJOLAIS' can be most closely compared to the *Sambucus* cultivars 'Gerda' (U.S. Plant Pat. No. 12,305) and 'Hyfsheen' (not patented). 'Gerda' differs from 'HYHOLAIS' in having foliage that is darker in color and less burgundy, foliage that is wider and less fine in texture, and flowers that are less visible and less defined in contrast. 'Hyfsheen' differs from 'HYFJOLAIS' in having flowers that are less visible and less defined in contrast, foliage that is wider and less fine in texture, and foliage that is lighter in color with a blue sheen.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales that fall within a one-year grace period prior to the filing date. Publications include listings on websites by Kordes Jungpflanzen, Genesis Plant Marketing, Cowell's Garden Center, Ashridge Nurseries, Spilkers Jungpflanzen, Baldur-Garten, Read Kong, Tradgardstrollet, Pinterest, Gabot, and Ihongtortai.

BRIEF DESCRIPTION OF THE DRAWINGS

The accompanying color photographs illustrate the overall appearance and distinct characteristics of the new *Sambucus*. The photographs were taken of a 3-year-old plant as grown outdoors in a 21-cm container in Bilsen, Germany.

The photograph in FIG. 1 provides a side view of the plant habit of 'HYFJOLAIS' in bloom.

Figure 1:
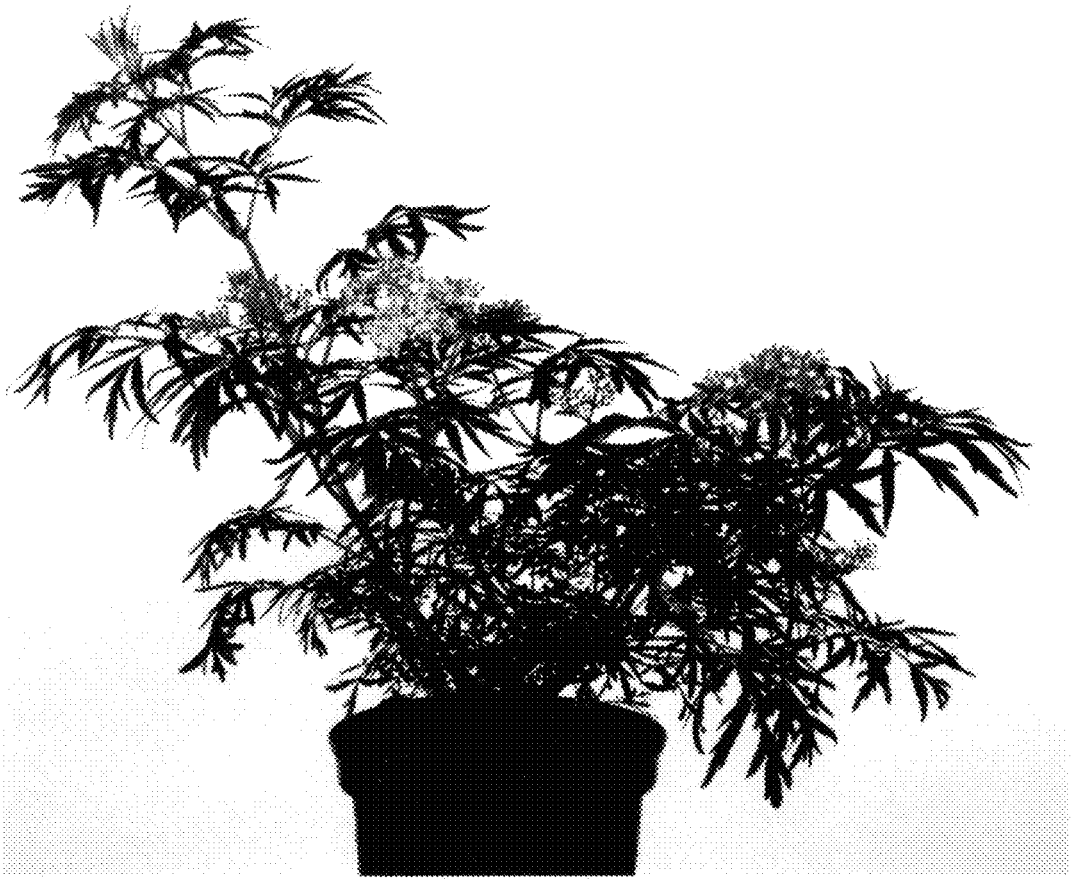
Figure 2:
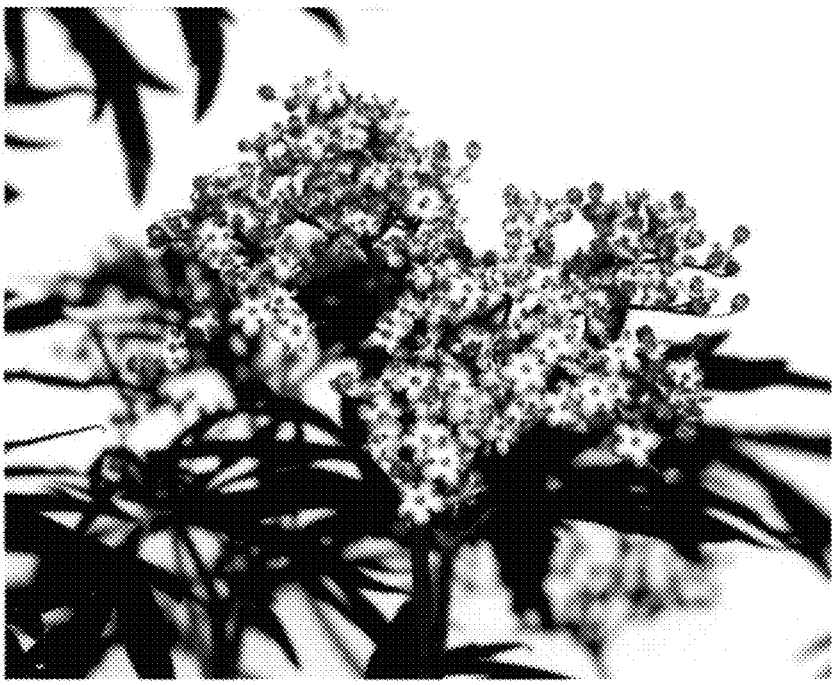

The photograph in FIG. 2 provides a close-up view of an inflorescence of 'HYFJOLAIS'.

Figure 3:
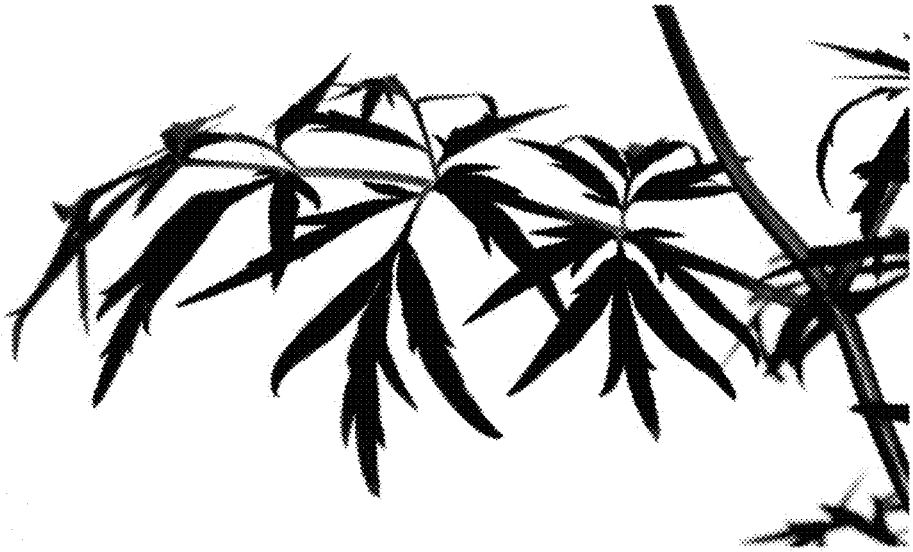

The photograph in FIG. 3 provides a close-up view of the foliage of 'HYFJOLAIS'.

The colors in the photographs are as close as possible with the photographic and printing technology utilized and the color values cited in the detailed botanical description accurately describe the colors of the new *Sambucus*.

BOTANICAL DESCRIPTION OF THE PLANT

The following is a detailed description of 3-year-old plants of the new cultivar as grown outdoors in 21-cm containers in Bilsen, Germany. Phenotypic differences may be observed with variations in environmental, climatic, and cultural conditions. The color determination is in accordance with The 2015 Colour Chart of The Royal Horticultural Society, London, England, except where general color terms of ordinary dictionary significance are used.

General description:

*Blooming period*.—May through June in The United Kingdom.

*Plant type*.—Deciduous shrub.

*Plant habit*.—Compact, broad, spreading.

*Height and spread*.—An average of 50.5 cm in height (soil level to top of foliar plane), 37 cm (soil to top of floral plane) and 68.5 cm in diameter as a plant 1.5 years in age in a container.

*Hardiness*.—At least in U.S.D.A. Zones 5 to 9.

*Diseases and pest resistance*.—No susceptibility or resistance to diseases or pests has been observed.

*Root description*.—Fibrous and fine, 165C in color.

*Growth rate*.—Moderately vigorous.

*Propagation*.—Softwood stem cuttings.

*Root development*.—About 3 weeks to initiate roots and 2 months to produce a young plant.

Branch description:

*Branch color*.—Young; 146C, angles tinged N199B, mature and internodes; a blend of N186C and 200A, tinged 146C, older stems and bark; 199B and 201B.

*Branch size*.—Up to 17.9 m in length and 4 mm in diameter.

*Stem shape*.—Angled with 6 sides.

*Stem quantity*.—An average of 6 main branches and 6 secondary branches per plant.

*Branch surface*.—Moderately glossy and moderately scabrous 156D in color.

*Branch aspect*.—Held at an average angle of 20° (varying between 60° and 110°).

*Branch habit*.—Moderately to freely branching.

*Branch strength*.—Moderately strong.

*Internode length*.—An average of 11.4 cm.

Foliage description:

*Leaf quantity*.—An average of 4 (2 pairs) per lateral branch.

*Leaflet quantity*.—An average of 7 leaflets per leaf.

*Leaf attachment*.—Petiolate.

*Leaf arrangement*.—Opposite.

*Leaf shape*.—Obovate.

*Leaf size*.—Whole leaf; an average of 17.5 cm in length, 13.6 cm in width, leaflet; 8.5 cm in length and 8.4 cm in width.

*Leaf shape*.—Whole leaf; obovate, leaflet; very broad ovate.

*Leaf base*.—Whole leaf and leaflet; attenuate.

*Leaf apex*.—Whole leaf and leaflet; acute to short apiculate.

*Leaf aspect*.—Slightly convex.

*Leaf venation*.—Pinnate, upper surface color; a blend of N186A and N186C, lower surface color; N186C.

*Leaf margin*.—Whole leaf and leaflet; deeply serrated to deeply incised and cleft.

*Leaflet surface*.—Whole leaf and leaflet; upper surface smooth, non-rugose, matte, glabrous, main vein moderately covered with very short hairs 0.4 mm in length, N155A in color, lower surface smooth, non-rugose, very slightly glossy, margins and main veins an average of 0.4 mm in length and N155A in color.

*Leaflet color*.—Young upper surface; N200A, young lower surface; N199B, apex tinged 200A, mature and fall upper surface; N186A and 203B, mature and fall lower surface; a blend of N200A and N200B.

*Petioles*.—4.7 cm in length and 0.3 mm in diameter, 200B, margined 146C in color, rounded in shape, strong, surface is sparsely covered with strigose hairs an average of 0.7 mm in length and N155A in color.

*Rachis*.—12.5 cm in length and 1.75 mm in diameter, 200B, margined 146C in color, rounded in shape, strong, surface is sparsely covered with strigose hairs an average of 0.7 mm in length and N155A in color.

Flower description:

*Inflorescence type*.—Compound, terminal cyme.

*Inflorescence size*.—Average of 4.4 cm in height, 10.4 cm in diameter.

*Flower fragrance*.—Sweet and pleasant.

*Flower lastingness*.—An average of 10 days.

*Flower buds*.—Spherical in shape, smooth, glabrous and matte surface, an average of 2.5 mm in diameter and height, 183C to 183D in color.

*Flower quantity*.—About 220 flowers per inflorescence, 1,760 flowers per plant.

*Flower size*.—7 mm in diameter and 3 mm in depth.

*Flower type*.—Rotate.

*Petals*.—5, sometimes 6, broadly ovate in shape, margins entire, base broadly cuneate, fused, 3 mm in length, 2.5 mm in width, broadly acute apex, upper and lower surface smooth, glabrous, matte, non-rugose, color; upper surface when opening and fully open; 155C, top 187D, lower surface when opening and fully open; 187C to 187D, base 186D.

*Sepals*.—5, rotate, ovate to triangular in shape, entire margin, acute apex, broad cuneate base, about 1 mm in length and 0.5 mm width, smooth, matte, and glabrous on upper and lower surface, color both surfaces; a blend of 183A and 200B.

*Peduncles*.—Terminal; rounded with flattened upper side in shape, held in a vertical angle, 8 cm in length and 3 mm in diameter, medium strength, slightly glossy surface, color 152C to 152D, tinged at the distal end 183B to 183C, secondary; rounded with flattened upper side in shape, held in an angle of 47.5°, 2.4 cm in length and 2 mm in diameter, medium strength, slightly glossy surface, color 183A.

*Calyx*.—Rotate, 0.5 mm in length, 3 mm in diameter.

*Pedicels*.—Rounded with flattened upper side in shape, 5 mm in length and 0.5 mm in diameter, smooth, glabrous, matte surface, color; 183C to 183D, tinged 148D.

Reproductive organs:

*Gynoecium*.—Pistils; average of 4, occasionally 2 to 3, 1 mm in length, style; 0.5 mm in length, 186A, stigma; 0.5 mm in length, obtuse in shape, 156C in color, ovary; 150D in color.

*Androecium*.—Stamens; 5, anthers; 1.25 mm in length, 1 mm in width, 179A in color, filaments; 1.5 mm in length, NN155D in color, pollen; low, 179C to 179D in color.

*Fruit and seed*.—No fruit or seed observed.

It is claimed:

1. A new and distinct cultivar of *Sambucus* plant named 'HYFJOLAIS' substantially as herein illustrated and described.

* * * * *